United States Patent [19]

Sung et al.

[11] 4,435,186
[45] Mar. 6, 1984

[54] ALCOHOL FUELS CONTAINING WEAR-INHIBITING AMOUNTS OF REACTION PRODUCTS OF AMINES AND PHOSPHATE ESTERS OF PHOSPHONIC ACIDS

[75] Inventors: Rodney L. Sung, Fishkill; Benjamin J. Kaufman; William M. Sweeney, both of Wappingers Falls, all of N.Y.

[73] Assignee: Texaco Inc., White Plains, N.Y.

[21] Appl. No.: 374,572

[22] Filed: May 3, 1982

[51] Int. Cl.$^3$ .................................................. C10L 1/26
[52] U.S. Cl. ............................................ 44/53; 44/56; 44/58; 44/72; 44/76; 260/501.12
[58] Field of Search ............... 44/53, 58, 72, 76, 56, 44/75; 123/1 A; 260/501.12, 925, 924; 252/387, DIG. 17, 174.16; 148/615 R

[56] References Cited

U.S. PATENT DOCUMENTS

| | | |
|---|---|---|
| 3,428,713 | 2/1969 | Bartlett et al. ...................... 260/925 |
| 3,505,044 | 4/1970 | Bartlett et al. ........................... 44/75 |
| 3,807,974 | 4/1974 | Kerley ..................................... 44/58 |
| 3,849,482 | 11/1974 | Christensen et al. ........... 260/501.12 |
| 4,145,382 | 3/1979 | Hayashi et al. ..................... 260/925 |
| 4,263,160 | 4/1981 | Morse ............................. 252/174.16 |
| 4,294,585 | 10/1981 | Sung ....................................... 44/53 |

Primary Examiner—Charles F. Warren
Assistant Examiner—Margaret B. Medley
Attorney, Agent, or Firm—Carl G. Ries; Robert A. Kulason; Carl G. Seutter

[57] ABSTRACT

A novel fuel composition contains ethanol or gasohol plus, as a wear-inhibiting additive, a quaternary ammonium reaction product of an amine

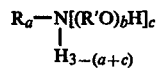

typically bis(2-hydroxyethyl)cocoamine and a phosphate, or phosphonic acid, typically dilauryl phosphate.

40 Claims, No Drawings

ALCOHOL FUELS CONTAINING
WEAR-INHIBITING AMOUNTS OF REACTION
PRODUCTS OF AMINES AND PHOSPHATE
ESTERS OF PHOSPHONIC ACIDS

FIELD OF THE INVENTION

This invention relates to alcohol products particularly characterized by decreased ability to corrode metal surfaces with which they come into contact.

BACKGROUND OF THE INVENTION

As is well known to those skilled in the art, alcohols such as ethanol may corrode metal surfaces with which they come into contact. This is particularly true of crude or commercially available ethanols which undesirably contain acidic components commonly acetic acid. In the case of fermentation alcohols, acetic acid may be present in amount of 0.003 w %–0.005 w % of the alcohol; and this may be responsible for the fact that the alcohol causes serious corrosion problems.

It is an object of this invention to provide a novel process for decreasing the corrosion of alcohol compositions. Other objects will be apparent to those skilled in the art.

STATEMENT OF THE INVENTION

In accordance with certain of its aspects, the novel composition of this invention may comprise (a) a major portion of a fuel containing (i) at least one alcohol selected from the group consisting of methanol and ethanol and (ii) gasoline in amount of 0–50 volumes per volume of alcohol; and (b) a minor effective wear-inhibiting amount of as wear-inhibiting agent a reaction product of (i) an amine

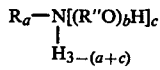

wherein R contains 1–30 carbon atoms and is selected from the group consisting of alkyl, alkenyl, alkaryl, aralkyl, cycloalkyl, and aryl hydrocarbon groups, R" is a divalent hydrocarbon group containing 1–30 carbon atoms and is selected from the group consisting of alkylene, alkenylene, alkarylene, aralkylene, cycloalkylene, and arylene hydrocarbon groups, a and c are each integers 1–2, a plus c is 2–3, and b is an integer 1–5; with (ii) a phosphate ester

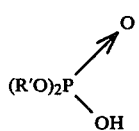

or a phosphonic acid

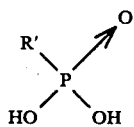

wherein R' contains 1–30 carbon atoms and is selected from the group consisting of alkyl, alkenyl, alkaryl, aralkyl, cycloalkyl, and aryl.

DESCRIPTION OF THE INVENTION

The fuel for internal combustion engines which may be treated by the process of this invention may contain (i) at least one alcohol selected from the group consisting of ethanol and methanol and (ii) gasoline in amount of 0–50 volumes per volume of alcohol. The fuel may be an alcohol-type fuel containing little or no hydrocarbon. Typical of such fuels are methanol, ethanol, mixtures of methanolethanol, etc. Commercially available mixtures may be employed. Illustrative of one such commercially available mixture may be that having the following typical analysis.

TABLE I

| Component | Parts |
|---|---|
| ethanol | 3157.2 |
| methyl isobutyl ketone | 126.3 |
| acetic acid | 0.256 |
| methyl alcohol | 0.24 |
| isopropyl alcohol | 0.2 |
| n-propyl alcohol | 0.162 |
| ethyl acetate | 0.2 |

The fuels which may be treated by the process of this invention include gasohols which may be formed by mixing 90–95 volumes of gasoline with 5–10 volumes of ethanol or methanol. A typical gasohol may contain 90 volumes of gasoline and 10 volumes of absolute alcohol.

It is preferred that the fuels to be treated by the process of this invention be substantially anhydrous i.e. that they contain less than about 0.3 v % water; typically they may contain 0.0001 v %–0.005 v %, say about 0.04 v % water.

It is a feature of these fuels that they may undesirably contain acidic contaminants which may cause serious corrosion problems. These contaminants are particularly in evidence when the alcohol is a commercially available alcohol which contains therein inter alia acids concurrently produced as by fermentation processes for producing ethanol or acids which have been picked up during handling. Acetic acid is a common acid present in the commercially available alcohols produced by fermentation; and it may be present in amount of 0.003 w %–0.005 w % of the total of the alcohol.

In accordance with practice of the process of this invention, there may be added to the fuel a minor wear-inhibiting amount of, as a wear-inhibiting additive, a quaternary ammonium reaction product of (i) an amine

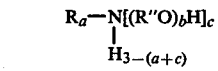

wherein R contains 1–30 carbon atoms and is selected from the group consisting of alkyl, alkenyl, alkaryl, aralkyl, cycloalkyl, and aryl hydrocarbon groups, R' is a divalent hydrocarbon group containing 1–30 carbon atoms and is selected from the group consisting of alkylene, alkenylene, alkarylene, aralkylene, cycloalkylene, and arylene hydrocarbon groups, a and c are each integers 1–2, a plus c is 2–3, and b is an integer 1–5 with (ii) a phosphonate ester or a phosphonic acid.

The amine reactants which may be employed in accordance with practice of the process of this invention, include those wherein R contains 1-30 carbon atoms selected from the group consisting of alkyl, alkenyl, alkaryl, aralkyl, cycloalkyl, and aryl groups and R" is a divalent hydrocarbon group containing 1-30 carbon atoms and is selected from the group consisting of alkylene, alkenylene, alkarylene, aralkylene, cycloalkylene, and arylene groups.

In the above compound, R may be a hydrocarbon radical selected from the group consisting of alkyl, aralkyl, cycloalkyl, aryl, alkaryl, and alkenyl, including such radicals when inertly substituted. When R is alkyl, it may typically be methyl, ethyl, n-propyl, iso-propyl, n-butyl, 1-butyl, sec-butyl, amyl, octyl, decyl, octadecyl, etc. When R is aralkyl, it may typically be benzyl, betaphenylethyl, etc. When R is cycloalkyl, it may typically be cyclohexyl, cycloheptyl, cyclcoctyl, 2-methylcycloheptyl, 3-butylcyclohexyl, 3-methylcyclohexyl, etc. When R is aryl, it may typically be phenyl, naphthyl, etc. When R is alkaryl, it may typically be tolyl, xylyl, etc. When R is alkenyl, it may typically be vinyl, allyl, 1-butenyl, etc. R may be inertly substituted i.e. it may bear a non-reactive substituent such as alkyl, aryl, cycloalkyl, ether, etc. Typically inertly substituted R groups may include 2-ethoxyethyl, carboethoxymethyl, 4-methyl cyclohexyl, etc. The preferred R groups may be alkyl group having 6-20 carbon atoms including eg hexyls, octyls, decyls, etc. R may preferably be a $C_6$-$C_{15}$ more preferably a $C_{13}$ straight chain alkyl-tridecyl.

R" is a divalent hydrocarbon group which may be selected from the same group as that from which R is selected but having one less hydrogen atom. Preferably R" is a $C_2$-$C_6$ group more preferably a $C_2$-$C_3$ group i.e. —$CH_2$—$CH_2$— or —$CH_2$—$CH_2$—$CH_2$.

In the formula, a, b, and c are integers. a may be 1-2. b may be 1-5, c may be 1-2. a plus c may be 2-3.

When a and c are each 1, the formula may be RNH[R"O)$_b$H] and the compositions may be typified by

TABLE

CocoNH($C_2H_4$O)H
$C_{12}H_{25}$NH($C_2H_4$O)H
$C_{10}H_{21}$NH(CHCH$_2$O)H
　　　　　　　　｜
　　　　　　　　CH$_3$ When a is 1 and c is 2, the formula may be R-N[(R"O)$_b$H]$_2$ and the compositions may be typified by

TABLE $C_{12}H_{25}$N[($C_2H_4$C)H]$_2$
$C_{12}H_{25}$N[($C_2H_4$O)H]$_2$

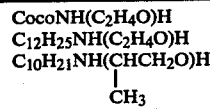

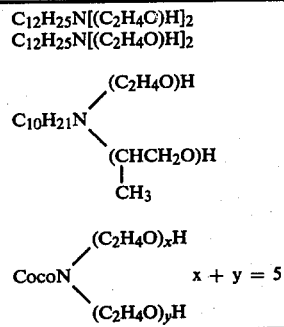

When a is 2 and c is 1, the formula may be R$_2$N[(R"O)$_b$H] and the compounds may be typified by

TABLE (C$_{10}$H$_{21}$)$_2$N(CHCH$_2$O)H
　　　　　　　　｜
　　　　　　　　CH$_3$ (C$_{12}$H$_{25}$)$_2$N(CH$_2$—CHO)H
　　　　　　　　　　｜
　　　　　　　　　　CH$_3$ (C$_{12}$H$_{25}$)$_2$N(CH$_2$CHO)H
　　　　　　　　｜
　　　　　　　　CH$_3$

The preferred compositions may be those wherein a is 1, b is 3, and c is 2. Preferably R" is —CH$_2$CH$_2$— or

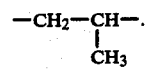

In the preferred embodiment R is coco i.e. the commercially available structure (derived from coco butter) and containing $C_{12}H_{25}$-hydrocarbon groups.

These compositions may be available commercially or they may be prepared as by known procedures.

Illustrative commercially available compositions may be the following, the first listed being a preferred composition:

TABLE

A. the Armak brand of bis(2-hydroxyethyl)cocoamine

Coco N(CH$_2$CH$_2$OH)$_2$

B. the Armak brand of polyoxyethylene (5) cocoamine

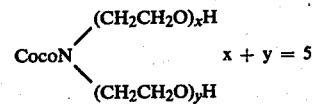

C. the Armak brand of bis(2-hydroxyethyl)octadecylamine

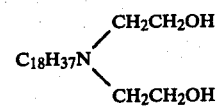

The phosphate ester (I) reactants or the phosphonic acid (II) reactants which may be employed may be characterized by the formulae

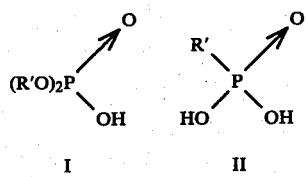

wherein R' contains 1-30, preferably 5-30, more preferably 10-18, say 14 carbon atoms and is selected from the group consisting of alkyl, alkenyl, alkaryl, aralkyl, cycloalkyl, and aryl hydrocarbon moieties.

In the above compound, R' may be a hydrocarbon radical selected from the group consisting of alkyl, aralkyl, cycloalkyl aryl, alkaryl, alkenyl, and alkynyl including such radicals when inertly substituted. When R' is alkyl, it may typically be methyl, ethyl, n-propyl, iso-propyl, n-butyl, i-butyl, sec-butyl, amyl, octyl, decyl, octadecyl, etc. When R' is aralkyl, it may typically be benzyl, beta-phenylethyl, etc. When R' is cycloalkyl, it may typically be cyclohexyl, cycloheptyl, cyclooctyl, 2-methylcycloheptyl, 3-butylcyclohexyl, 3-methylcyclohexyl, etc. When R' is aryl, it may typically be tolyl, xylyl, etc. When R' is alkenyl, it may typically be vinyl, allyl, 1-butenyl, etc. When R' is alkynyl, it may typically be ethynyl, propynyl, butynyl, etc. R' may be inertly substituted i.e. it may bear a non-reactive substituent such as alkyl, aryl, cycloalkyl, ether, halogen, nitro, etc. Typically inertly substituted R' groups may include 3-chloropropyl, 2-ethoxyethyl, carboethoxymethyl, 4-methyl cyclohexyl, p-chlorophenyl, p-chlorobenzyl, 3-chloro-3-methylphenyl, etc. The preferred R' groups may be alkyl group, containing 10-18 carbon atoms. R' may preferably be $C_{14}$, a tetradecyl group when the compound is a phosphonic acid, and $C_{12}$ lauryl when the compound is a phosphate.

These phosphates or phosphonic acids may be readily available or they may be prepared—typically in the case of the phosphonic acids by the reaction of olefins with phosphites. In a typical reaction, one gram mole of tetradecene may be reacted with 1.5 gram moles of dimethyl phosphite and a catalytic amount (4 g) of ditertiary-butyl peroxide. The mixture is heated at 150° C. for 4 hours. After cooling, aqueous hydrochloric acid is added and the mixture extracted with toluene solvent. The solvent mixture is separated and toluene is stripped off to leave the 1:1 adduct—typically tetradecane phosphonic acid.

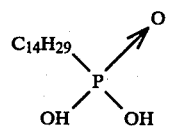

Illustrative phosphonic acids which may be employed may include:

| TABLE | |
|---|---|
| tetradecane | phosphonic acid |
| decane | phosphonic acid |
| dodecane | phosphonic acid |
| nonane | phosphonic acid |

Illustrative phosphate esters which may be employed may include:

| TABLE | |
|---|---|
| tetradecyl | phosphate |
| decyl | phosphate |
| dodecyl | phosphate |

Preparation of the quaternary products of this invention may be carried out typically by reacting one mole of the phosphate ester or the phosphonic acid with one mole of the ether-amine.

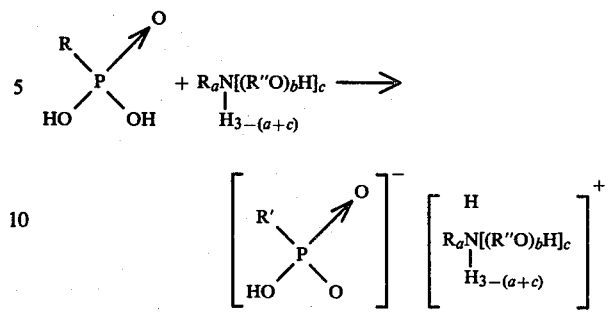

The product may be further reacted with another mole (bimolar amounts in total) of amine to yield the bimolar product.

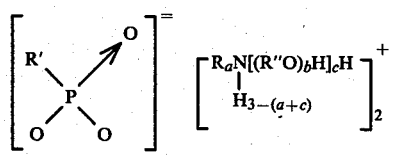

Similar reactions may be carried out with the phosphate esters.

Reaction may be carried out typically by reacting equivalent quantities of reactants in a reaction operation at 20° C.–100° typically 20° C.–50° C., say 25° C. or ambient temperature and 0–500 psig, typically 0–100 psig, say atmospheric pressure for 0.1–4 hours, say 0.75 hours. If desired, reaction may be carried out in the presence of an excess of absolute alcohol, preferably ethanol, or hydrocarbon, typically toluene or xylene or isooctane. Reaction product may be employed without further purification.

Typical reaction products may include:

TABLE

A $\left[\begin{array}{c} C_{14}H_{29} \diagdown P \diagup O \\ HO \diagup \diagdown O \end{array}\right]^{-}$ $[Coco-N-(CH_2CH_2OH)_2]^+$ B $\left[\begin{array}{c} C_{14}H_{29} \diagdown P \diagup O \\ O \diagup \diagdown O \end{array}\right]^{=}$ $\left[\begin{array}{c} Coco-N-(CH_2CH_2OH)_2 \\ | \\ H \end{array}\right]^+_2$ C $\left[\begin{array}{c} C_{12}H_{25} \diagdown P \diagup O \\ HO \diagup \diagdown O \end{array}\right]^{-}$ $[Coco-N-(CH_2CH_2OH)_2]^+$ D $\left[\begin{array}{c} C_{12}H_{25} \diagdown P \diagup O \\ O \diagup \diagdown O \end{array}\right]^{=}$ $[Coco-N-(CH_2CH_2OH)_2]^+_2$ TABLE-continued E $$\left[ (C_{14}H_{29}O)_2-P \underset{O}{\overset{O}{\diagup}} \right]^- \left[ C_{12}H_{25}-\underset{H}{\overset{|}{N}}-(CH_2CH_2OH)_2 \right]^+$$

The so-prepared anti-wear additives may be added to fuels (including alcohol, gasoline, gasohol etc.) or to antifreeze. These compositions may be particularly found to be effective when added to absolute alcohol fuels typified by those available commercially containing compounds including ethers, esters, acids, etc.

The so-prepared anti-wear additives may be added to a fuel in minor wear-inhibiting amount of about 0.003–10 w % preferably 0.01–6 w %, more preferably 0.2–3 w %, say 1 w %. Larger amounts may be employed but may not be necessary.

It is a feature of this invention that the fuel composition so prepared is characterized by its increased ability to significantly reduce scar diameters (wear) in the Four-Ball Wear Test.

The Four Ball Wear Test is carried out by securely clamping three highly polished steel balls (each 0.5 inch in diameter) in a test cup in an equilateral triangle in a horizontal plane. The fourth highly polished steel ball, resting on the three lower balls to form a tetrahedron, is held in a chuck. A weight lever arm system applies weight to the test cup, and this load holds the balls together. In the standard test, the speed of rotation is 1800 rpm; the load is 5 kilograms. The assembly is submerged in the liquid to be tested. The standard test is carried out at ambient temperature for 30 minutes. As the chuck and upper ball rotate against the fixed lower balls, the friction of the upper ball rotating in relation to the lower balls produces a wear-scar, the diameter of which (i.e. the depth along a diameter of the ball) is measured. The average of the wear on the three lower balls is the rating assigned (in millimeters).

It is observed that the use of the technique of this invention permits reduction in the average scar diameter by as much as 25%–35%. A reduction of 10% is a significant reduction.

DESCRIPTION OF PREFERRED EMBODIMENTS

Practice of this invention will be apparent to those skilled in the art from the following examples wherein, as elsewhere in this specification, all parts are parts by weight unless otherwise specified.

EXAMPLE I

In this example which illustrates the best mode known to me of practicing the process of this invention, there is added to a reaction vessel 21.8 parts of dilauryl phosphate and 28 parts of the Armak brand of Ethomeen C/15

$$CocoN \underset{(CH_2CH_2O)_yH}{\overset{(CH_2CH_2O)_xH}{\diagdown}} \quad \text{wherein } x+y=5$$

This corresponds to a 1:1 mole ratio. The mixture is agitated at room temperature of 25° C. for 0.75 hours.

A test formulation is made up containing the alcohol of Table I supra plus 1 w % of the above reaction product. This formulation was subjected to the four-ball test. The Average Scar Diameter was 0.18 mm.

EXAMPLE II*

In this control Example, the test procedure of Example I is carried out with no additive i.e. the medium tested is alcohol containing no additive. The Average Scar Diameter is 0.4775 mm.

TABLE

| Example | Average Scar Diameter |
|---|---|
| I | 0.18 mm |
| II | 0.4775 |

It is apparent that use of the preferred embodiment of this invention (Example I) desirably increased the wear-inhibiting property of the alcohol by (0.4775/0.18) or 265%.

Results comparable to Example I may be attained if the additive is

TABLE

| Example | Additive |
|---|---|
| IV | Ethomeen c/12.dilauryl phosphate |
| V | Ethomeen c/20.dilauryl phosphate |
| VI | bis(hydroxyethyl) octadecylamine.dilauryl phosphate |
| VII | bis(hydroxyethyl) tallowamine.dilauryl phosphate |

The Ethomeen c/12 composition has the same formula as the composition of Example I except $x+y=2$, i.e. the compound is bis(2-hydroxyethyl) cocoamine. The Ethomeen c/20 composition has the same formula as the composition of Example I except $x+y=10$.

Results comparable to those of Example I may be obtained if the fuel is as follows:

TABLE

| Example | Fuel |
|---|---|
| VIII | absolute methanol |
| IX | Gasohol containing 90 v % gasoline and 10 v % absolute ethanol |

Although this invention has been illustrated by reference to specific embodiments, it will be apparent to those skilled in the art that various changes and modifications may be made which clearly fall within the scope of this invention.

We claim:

1. A fuel composition for internal combustion engines comprising
   (a) a major portion of a fuel containing (i) at least one alcohol selected from the group consisting of ethanol and methanol and (ii) gasoline in amount of 0–50 volumes per volume of alcohol; and
   (b) a minor wear-inhibiting amount 0.2–10 w % of, as a wear-inhibiting additive, a reaction product of
   (i) an amine $$R_a-\underset{H_{3-(a+c)}}{\overset{|}{N}}[(R''O)_bH]_c$$

wherein R contains 1–30 carbon atoms and is selected from the group consisting of alkyl, alkenyl, alkaryl, aralkyl, cycloalkyl, and aryl hydrocarbon groups, R″ is a divalent hydrocarbon group containing 1-30 carbon atoms and is selected from the group consisting of alkylene, alkenylene, alkarylene, aralkylene, cycloalkylene, and arylene hydrocarbon groups, a and c are each integers 1-2, a plus c is 2-3, and b is an integer 1-5 with
(ii) a phosphate ester

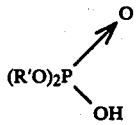

or a phosphonic acid

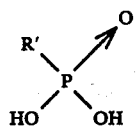

wherein R' contains 1-30 carbon atoms and is selected from the group consisting of alkyl, alkenyl, alkaryl, aralkyl, cycloalkyl, and aryl.

2. A fuel composition for internal combustion engines as claimed in claim 1 wherein said fuel is an alcohol.

3. A fuel composition for internal combustion engines as claimed in claim 1 wherein said fuel is methanol.

4. A fuel composition for internal combustion engines as claimed in claim 1 wherein said fuel is ethanol.

5. A fuel composition for internal combustion engines as claimed in claim 1 wherein said fuel is a commercial ethanol.

6. A fuel composition for internal combustion engines as claimed in claim 1 wherein said fuel is a commercial ethanol containing acid.

7. A fuel composition for internal combustion engines as claimed in claim 1 wherein said fuel is a commercial ethanol containing acetic acid.

8. A fuel composition for internal combustion engines as claimed in claim 1 wherein said fuel is a gasohol.

9. A fuel composition for internal combustion engines as claimed in claim 1 wherein said fuel is substantially anhydrous.

10. A fuel composition for internal combustion engines as claimed in claim 1 wherein said fuel contains less than 0.3 v % water.

11. A fuel composition as claimed in claim 1 wherein said amine is

RNH[(R″O)$_b$H].

12. A fuel composition as claimed in claim 11 wherein R″ is —CH$_2$CH$_2$—.

13. A fuel composition as claimed in claim 11 wherein R″ is

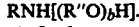

14. A fuel composition as claimed in claim 11 wherein R is a straight chain alkyl.

15. A fuel composition as claimed in claim 11 wherein R is tri-decyl.

16. A fuel composition as claimed in claim 11 wherein R is coco.

17. A fuel composition as claimed in claim 11 wherein said amine is

Coco NH(C$_2$H$_4$O)H.

18. A fuel composition as claimed-in claim 11 wherein said amine is

RN[(R″O)$_b$H]$_2$.

19. A fuel composition as claimed in claim 1 wherein said amine is

RN[R″OH]$_2$.

20. A fuel composition as claimed in claim 19 wherein said amine is

C$_{12}$H$_{25}$N[C$_2$H$_4$OH]$_2$.

21. A fuel composition as claimed in claim 19 wherein said C$_{12}$H$_{25}$N[(CH$_2$CH$_2$O)$_b$H]$_2$ wherein b is 1-5.

22. A fuel composition as claimed in claim 11 wherein said amine is

R$_2$N[(R″O)$_b$H].

23. A fuel composition as claimed in claim 22 wherein R″ is —CH$_2$—CH$_2$—.

24. A fuel composition as claimed in claim 22 wherein said R″ is

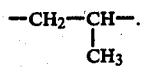

25. A fuel composition as claimed in claim 22 wherein R is a straight chain alkyl.

26. A fuel composition as claimed in claim 22 wherein R is tri-decyl.

27. A fuel composition as claimed in claim 22 wherein R is coco.

28. A fuel composition as claimed in claim 22 wherein said amine is (Coco)$_2$N[(CH$_2$CH$_2$O)$_b$H].

29. A fuel composition as claimed in claim 1 wherein the phosphonic acid contains 5-40 carbon atoms.

30. A fuel composition as claimed in claim 1 wherein the phosphonic acid is tetradecane phosphonic acid.

31. A fuel composition as claimed in claim 1 wherein the amine and the phosphorus compound are reacted in substantially equimolar quantities.

32. A fuel composition as claimed in claim 1 wherein the amine and the phosphorus compound are reacted in mole ratio of one phosphorus compound:two amine.

33. A fuel composition comprising
a major portion of a fuel containing (i) at least one of ethanol and methanol and (ii) gasoline in amount of 0-50 volumes per volume of alcohol; and
(i) 0.2-10 w% of the reaction product of

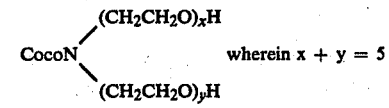 wherein x + y = 5 and
(ii) an equimolar amount of tetradecane phosphonic acid.

34. A fuel composition comprising
a major portion of a fuel containing (i) at least one of ethanol and methanol and (ii) gasoline in amount of 0-50 volumes per volume of alcohol; and
(i) 0.2-10 w% of the reaction product of

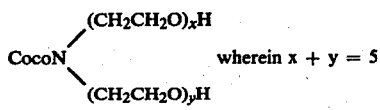

and (ii) a bimolar amount of dodecane phosphonic acid.

35. The method of improving the wear-resistance properties of a fuel containing at least one alcohol selected from the group consisting of ethanol and methanol and 0–50 volumes of gasoline per volume of alcohol which comprises adding to said fuel a minor, wear-inhibiting amount of 0.2–10 w% of the reaction product of (i) an amine

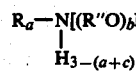

wherein R contains 1–30 carbon atoms and is selected from the group consisting of alkyl, alkenyl, alkaryl, aralkyl, cycloalkyl, and aryl hydrocarbon groups, R" is a divalent hydrocarbon group containing 1–30 carbon atoms and is selected from the group consisting of alkylene, alkenylene, alkarylene, aralkylene, cycloalkylene, and arylene hydrocarbon groups, a and c are each integers 1–2, a plus c is 2–3, and b is an integer 1–5, with (ii) a phosphate ester

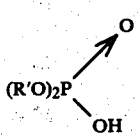

or a phosphonic acid

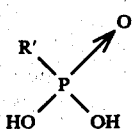

wherein R' contains 1–30 carbon atoms and is selected from the group consisting of alkyl, alkenyl, alkaryl, aralkyl, cycloalkyl, and aryl.

36. A novel composition comprising the reaction product of (i) an amine

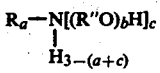

wherein R contains 1–30 carbon atoms and is selected from the group consisting of alkyl, alkenyl, alkaryl, aralkyl, cycloalkyl, and aryl hydrocarbon groups, R" is a divalent hydrocarbon group containing 1–30 carbon atoms and is selected from the group consisting of alkylene, alkenylene, alkarylene, aralkylene, cycloalkylene, and arylene hydrocarbon groups, a and c are each integers 1–2, a plus c is 2–3, and b is an integer 1–5 with (ii) phosphonic acid

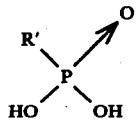

wherein R' contains 1–30 carbon atoms and is selected from the group consisting of alkyl, alkenyl, alkaryl, aralkyl, cycloalkyl, and aryl.

37. A novel composition as claimed in claim 36 wherein said phosphonic acid is

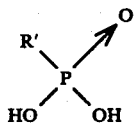

wherein R' is a $C_{10}$–$C_{18}$ alkyl group.

38. A novel composition as claimed in claim 36 wherein said phosphonic acid is

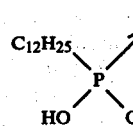

39.

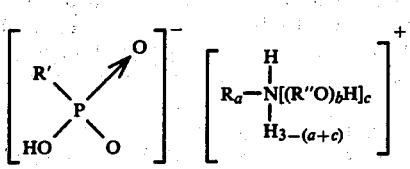

wherein R contains 1–30 carbon atoms and is selected from the group consisting of alkyl, alkenyl, alkaryl, aralkyl, cycloalkyl, and aryl groups, R" is divalent hydrocarbon group containing 1–30 carbon atoms selected from the group consisting of alkylene, alkenylene, alkarylene, aralkylene, cycloalkylene, and arylene, and R' contains 1–30 carbon atoms and is selected from the group consisting of alkyl, alkaryl, aralkyl, alkenyl, cycloalkyl, and aryl, a and c are each integers 1–2, a plus c is 2–3, and b is an integer 1–5.

40.

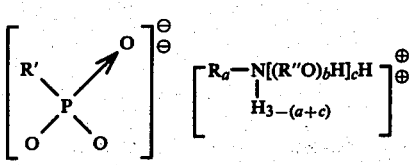

wherein R contains 1–30 carbon atoms and is selected from the group consisting of alkyl, alkenyl, alkaryl, aralkyl, cycloalkyl, and aryl groups, R" is divalent hydrocarbon group containing 1–30 carbon atoms selected from the group consisting of alkylene, alkenylene, alkarylene, aralkylene cycloalkylene, and arylene, and R' contains 1–30 carbon atoms and is selected from the group consisting of alkyl, alkaryl, aralkyl, alkenyl, cycloalkyl, and aryl, a and c are each integers 1–2, a plus c is 2–3, and b is an integer 1–5.

* * * * *

UNITED STATES PATENT AND TRADEMARK OFFICE
CERTIFICATE OF CORRECTION

PATENT NO.  : 4,435,186
DATED       : 3/6/84
INVENTOR(S) : R. L. Sung et al

It is certified that error appears in the above—identified patent and that said Letters Patent is hereby corrected as shown below:

Cover sheet: In the penultimate line of the Title, cancel "OF", insert -- OR --;

Column 1, line 5, cancel "OF", insert -- OR --;

Column 4, insert as the first entry in the table $-- (C_{12}H_{25})_2 \ N \ (C_2H_4O) \ H --$;

Column 4, line 10, cancel the third formula in the Table which incorrectly duplicates the second entry;

Column 10, line 17, after "said", insert -- amine is --.

Signed and Sealed this

Ninth Day of October 1984

[SEAL]

Attest:

GERALD J. MOSSINGHOFF

Attesting Officer

Commissioner of Patents and Trademarks